(12) United States Patent
Greene et al.

(10) Patent No.: US 6,180,772 B1
(45) Date of Patent: *Jan. 30, 2001

(54) NUCLEIC ACIDS ENCODING DOMINANT NEGATIVE I-κ-B -α POLYPEPTIDES

(75) Inventors: Warner C. Greene, Hillsborough, CA (US); Shao-Cong Sun, Hershey, PA (US); Parham Ganchi, Brookline, MA (US)

(73) Assignee: J. David Gladstone Institutes, San Francisco, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/064,713

(22) Filed: Apr. 22, 1998

Related U.S. Application Data

(62) Division of application No. 08/606,190, filed on Feb. 23, 1996, now abandoned.

(51) Int. Cl.$^7$ ..................................................... C12N 15/12
(52) U.S. Cl. ............................................................. 536/23.5
(58) Field of Search ................................. 536/23.1, 23.5; 530/350

(56) References Cited

PUBLICATIONS

Hatada et al, The EMBO Journal, vol. 12(7): pp. 2781–2788, 1993.*

Ernst et al, Molecular and Cellular Biology, vol. 15(2): pp. 872–882, Jan. 23, 1995.*

Brockman, et al., "Coupling of a Signal Response Domain in IκB–α to Multiple Pathways for NF–κB Activation", *Mol. Cell. Biol.* 15: 2809–2818 (1995).

Brown, et al., "Control of IκB–α Proteolysis by Site–Specific, Signal–Induced Phosphorylation", *Science* 267: 1485–1487 (1995).

Orkin, et al., "Report and Recommendation of the Panel to Assess the NIH Investment in Research on Gene Therapy", unnumbered pages, (1995).

Rodriquez, M.S., et al., "Inducible Degradation of IκBα In Vitro and In Vivo Requires the Acidic C–Terminal Domain of the Protein", *Mol. Cell. Biol.* 15(5): 2413–2419 (1995).

Siebenlist, et al., "Structure, Regulation and Function of Nf–κB", *Annu. Rev. Cell. Biol.* 10: 405–455 (1994).

Traenckner, E.B., et al., "Phosphorylation of human IκB–α on serines 32 and 36 controls IκB–α proteolysis and NF–κB activation in response to diverse stimuli," *EMBO J.* 14(12): 2876–2883 (1995).

Whiteside, S.T., et al., "N–and C–Terminal Sequences Control Degradation of MAD3/IκBα in Response to Inducers of NF–κB Activity," *Mol. Cell. Biol.* 15(10): 5339–5345 (1995).

* cited by examiner

*Primary Examiner*—Terry McKelvey
(74) *Attorney, Agent, or Firm*—Townsend and Townsend and Crew, LLP

(57) ABSTRACT

Methods and compositions for the inhibition of NF-κB activation are disclosed.

5 Claims, 10 Drawing Sheets

US 6,180,772 B1

NUCLEIC ACIDS ENCODING DOMINANT NEGATIVE I-κ-B-α POLYPEPTIDES

CROSS-REFERENCE TO RELATED APPLICATONS

This application is a division of and claims the benefit of U.S. application Ser. No. 08/606,190, filed Feb. 23, 1996, now abandoned, the disclosure of which is incorporated by reference.

BACKGROUND OF THE INVENTION

Nuclear factor κB (NF-κB) is a eukaryotic transcription factor that exerts pleiotropic effects on diverse cellular genes involved in the immediate early steps of immune activation and inflammation. Additionally, NF-κB has been implicated in the transcriptional activation of several viruses, including HIV-1 (for a review, see Siebenlist et al. *Annu. Rev. Cell. Biol.* 10:405–455 (1994)).

Nuclear expression and consequent biological action of the eukaryotic NF-κB transcription factor complex is tightly regulated through its cytoplasmic retention by an ankyrin-rich inhibitory protein termed IκBα. IκBα specifically binds to and masks the nuclear localization signal of the Rel A subunit of NF-κB, thereby effectively sequestering this transcription factor complex in the cytoplasm. Specific cellular activation signals lead to the rapid proteolytic degradation of IκBα and the concomitant nuclear translocation of NF-κB. Such signals include, for example, mitogens such as phorbol esters, cytokines such as tumor necrosis factor alpha (TNF-α) and interleukin-1 (IL-1), and the Tax protein from the type I human T cell leukemia virus (HTLV-1). Activation of NF-κB by these and other inducers appears to involve the transient phosphorylation and subsequent proteolytic degradation of IκBα which permits nuclear translocation of the liberated NF-κB complex. Nuclear expression of the NF-κB complex leads to transcriptional activation of a broad array of cellular genes involved in immune stimulation, inflammation, and cell growth.

Mutant IκBα molecules have been constructed to investigate the regions in IκBα essential for signaling and degradation (Brown et al. *Science* 267:1485–1487 (1995); Brockman et al. *Mol. Cell. Biol.* 15:2809–2818 (1995)).

SUMMARY OF THE INVENTION

A class of dominant negative IκBα mutants was constructed that retains full inhibitory function on NF-κB yet fails to undergo stimulus induced degradation. These mutants can be used to inhibit NF-κB activation in specific target cells, thereby reducing or eliminating undesirable consequences of NF-κB activation.

One aspect of the invention is a method of inhibiting NF-κB activation in a cell comprising introducing into the cell nucleic acid encoding a dominant negative mutant IκBα polypeptide, wherein the IκBα mutant polypeptide is expressed in the cell.

A further aspect of the invention is a composition comprising an IκBα polypeptide, wherein residues 1 through 36 and 278–317 are deleted.

Human Jurkat T cells were transfected with either the parental pCMV4 vector or cDNA expression vectors encoding either Rel A alone or Rel A and the indicated IκBα wild-type or deletion mutants. These cells were also transfected with a luciferase reporter plasmid containing the HIV-1 κB enhancer (κB-TATA-luc). Luciferase activity was measured after 48 hr of transfection and are presented as the relative fold-induction over basal levels obtained with cells transfected with pCMV4 alone (column 1). The values shown represent the means±SEM obtained in three independent experiments.

Figure 6:
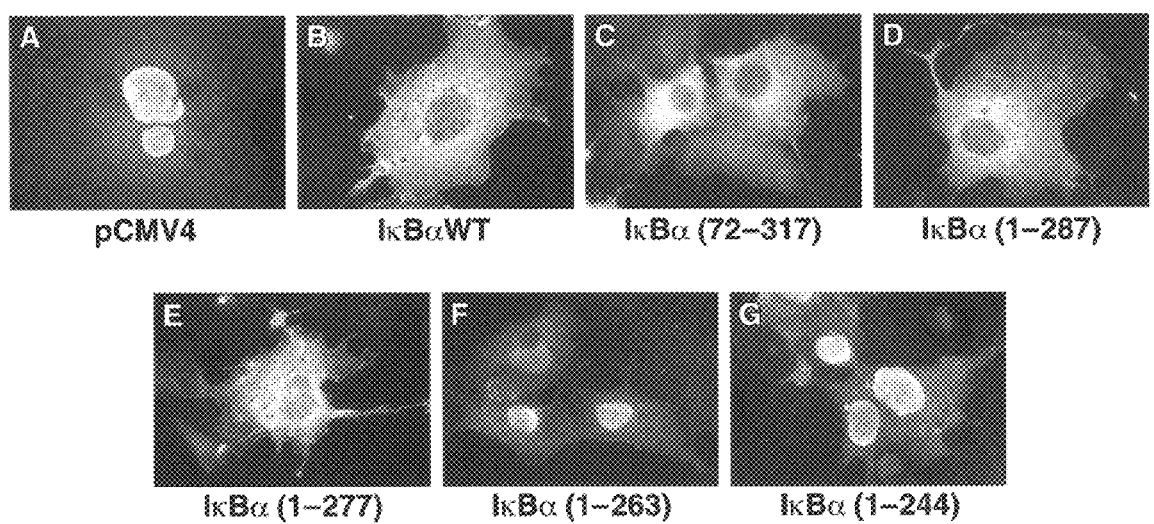

FIG. 6 depicts immunofluorescence assays of COS7 cells co-transfected with Rel A C-terminal truncation mutant, p65(1–312) which assembles normally with IκBα, and either the parental pCMV4 vector or the indicated wild-type or mutant IκBα expression vectors. After 48 hr, the transfected cells were subjected to indirect immunofluorescence assay using Rel A-specific antisera and Texas red-conjugated anti-rabbit Ig secondary antibody. Principally cytoplasmic patterns of Rel A staining are seen in panels B, C, and D while nuclear staining is seen in panels A, F, and G. A whole cell pattern of staining is seen in panel E.

Figure 7:
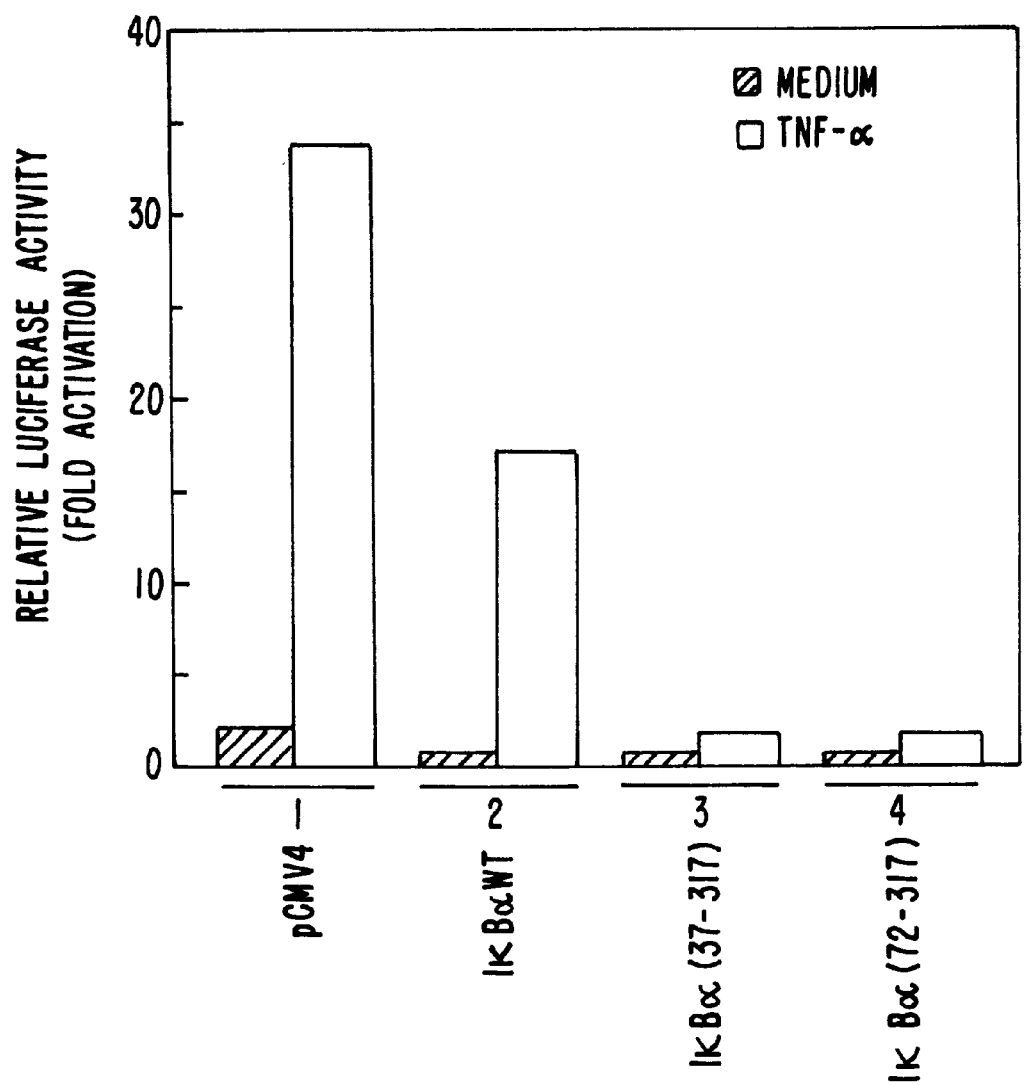

FIG. 7 is a graph depicting relative luciferase activity in human Jurkat cells transfected with either the parental vector pCMV4 or the indicated wild-type and N-terminally truncated IκBα cDNA expression vectors, and a luciferase reporter plasmid containing the HIV-1 κB enhancer. After 48 hr. the cells were stimulated with TNF-α (10 ng/ml) for 5 hr and the cells then collected for luciferase assay. Luciferase activity is presented as the relative fold-induction over the basal level obtained in cells transfected with pCMV4 alone (not shown). Similar results were obtained in two additional experiments.

Figure 8:
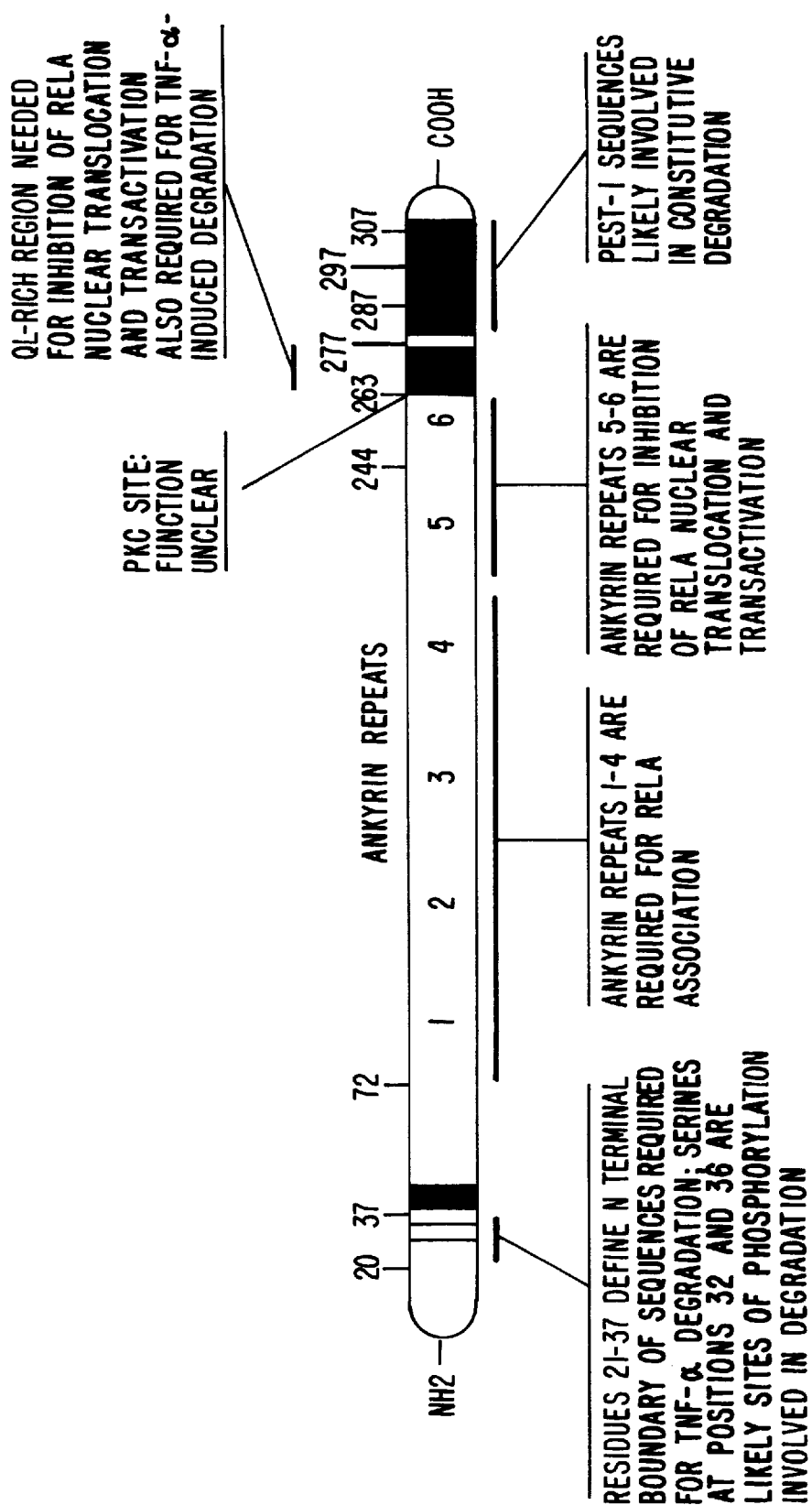

FIG. 8 is a schematic summary of various functional domains identified within IκBα.

DESCRIPTION OF THE PREFERRED EMBODIMENTS

As used herein, a dominant negative mutant of IκBα is defined as an IκBα polypeptide that retains full inhibitory function of NK-κB yet fails to undergo stimulus induced degradation. The scope of the invention is intended to include nucleic acid encoding such mutant polypeptides and nucleic acid which hybridizes to nucleic acid encoding such mutant polypeptides.

Mutants can be constructed by techniques well known in the art to generate the desired phenotype. The nucleotide and amino acid sequences of the IκBα gene are described in Haskill et al. Cell 65:1281–1289 (1991). Preferably, at least ser32 or ser36, more preferably both ser32 and ser36, are deleted or substituted (for example, by substitution with alanine).

Typically, such mutants are constructed as deletions of the N-terminal region of the IκBα gene through at least ser32, more preferably, through ser36. Apart from truncation of the N-terminus, one or both of these serine residues can be removed by smaller, internal deletions in the N-terminus. Deletions of the N-terminus can extend through residue 71.

Further alterations in the IκBα polypeptide are also possible. For example, in addition to substitution or deletion of the N-terminus, deletion of the C-terminus from residue 278 through residue 317 can be incorporated into the mutant. Any residues in the C-terminal region 278 through 317 can also be altered in the mutant.

The definition of dominant negative mutant IκBα polypeptide is intended to include any further variants within the region 72–278 which retain this phenotype.

Nucleic acid encoding the dominant negative IκBα mutant can be introduced into a specific, desired cell type in a variety of ways known in the art. Typically, the nucleic acid is incorporated into a vector containing appropriate signals for expression of the IκBα coding sequence. The vector and the signals for expression are chosen on the basis of the target cell. For example, in some instances an inducible expression system is preferred, while in others constitutive expression is preferred. Expression systems of both sorts are well known in the art.

The cell population targeted can include lymphocytes, tumor cells, specific cell types involved in inflammation, and so on. Delivery to the targeted cell type can occur in vivo or in vitro. For example, the IκBα mutants can be incorporated into vectors, such as retroviral vectors, that specifically infect certain cell subpopulations having certain receptors. Similarly, the IκBα mutants can be incorporated in expression vectors that are packaged into liposomes that can fuse with desired cell types.

Examples of delivery and expression systems are reviewed in, for example, Hanania et al. *American Journal of Medicine,* 99N5:537–552 (1995); Smith, *Ann. Rev. Microb.* 49:807–838 (1995); Brenner, *J. Internal Med.,* 237:229–239 (1995).

Depending on the system used, the vector can be administered to the host, usually a mammal, preferably a human, by usual routes of administration of pharmaceuticals, such as parenteral, intravenous, intranasal, douche, enema, etc. In some embodiments, the target cells can be isolated from the host, transformed with the IκBα expression vectors by a number of techniques known in the art, then returned to the body, as for example, with tissue samples and cells from blood or other body fluids.

In yet further embodiments, the vector can be administered into a particular location, such as a joint, for the treatment of inflammation. (See, for example, Auphen et al. *Science* 270:287–286 (1995).)

In a further example, dominant negative IκBα mutants can be used as inhibitors of HIV replication. In this instance, expression of a dominant negative IκBα mutant would be placed under the control of an HIV LTR. Thus, only in cells infected with HIV would the dominant negative IκB mutant be expressed. The expressed mutant protein would at least inhibit TNF-α induced activation of the HIV κB enhancer, thereby inhibiting replication of the virus.

In a further example, dominant negative mutants of IκBα can be used to inhibit activation of T cells or macrophages in hosts having abnormal states of immune activation. Preferably, such expression systems would be inducible and reversible.

EXAMPLE

Geheration and Characterization of IκBα Mutants

Figure 1:
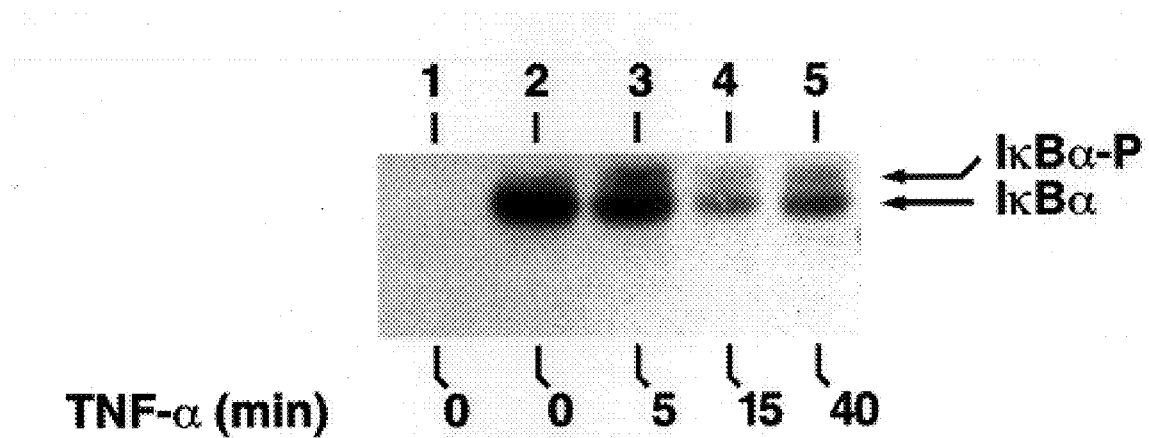
FIG. 1 depicts TNF-α induced degradation of exogenously expressed IκBα in HeLa cells. HeLa cells were transfected with either the parental vector pCMV4-3HA (lane 1) or a cDNA expression vector encoding the HA-IκBα fusion protein (lanes 2–5). These cells were subsequently stimulated with human TNF-α (20 ng/ml) for the indicated time periods, followed by the isolation of cellular extracts. Approximately 15 μg of each extract was then subjected to SDS-PAGE separation and immunoblotting using a monoclonal antibody specific for the HA epitope tag (anti-HA). Phosphorylated (IκBα-P) and basal forms of IκBα are indicated.

Basically, to explore sequence elements within IκBα that regulate its inducible degradation, an in vivo system was identified that permitted detection of stimulus coupled degradation of transiently expressed exogenous IκBα molecules. This system involved the use of HeLa cells, TNF-α as the inducing agent, and lipofectamine mediated transfection of wild type or mutant IκBα expression vectors. To distinguish the transfected gene product from endogenous IκB, an influenza hemagglutinin (HA) epitope tag was incorporated into the various IκBα expression vectors. Extracts were prepared from these transiently transfected cells at various times after TNF-α addition (0–40 minutes)

and analyzed for IκBα expression by immunoblotting with a monoclonal antibody specific for the HA epitope tag (anti-HA, Babco, Berkeley, Calif.). As shown in FIG. 1, the anti-HA antibody specifically reacted with a 40 KD protein species present in cells transfected with the HA-IκBα vector (lane 2) but lacking in cells transfected with the parental CMV4 vector (lane 1). This 40 KD protein also reacted with an IκBα specific antiserum. Thus, the anti-HA antibody specifically recognized the transfected, but not the endogenous IκBα. Importantly, as observed with the endogenously synthesized IκBα, TNF-α stimulation of the transfected cells led to the rapid degradation of the transfected wild type HA-IκBα (lanes 3–5). Moreover, the degradation of IκBα was preceded by the appearance of a more slowly migrating IκBα species known to be a phosphorylated form of this inhibitor.

Figure 2A:
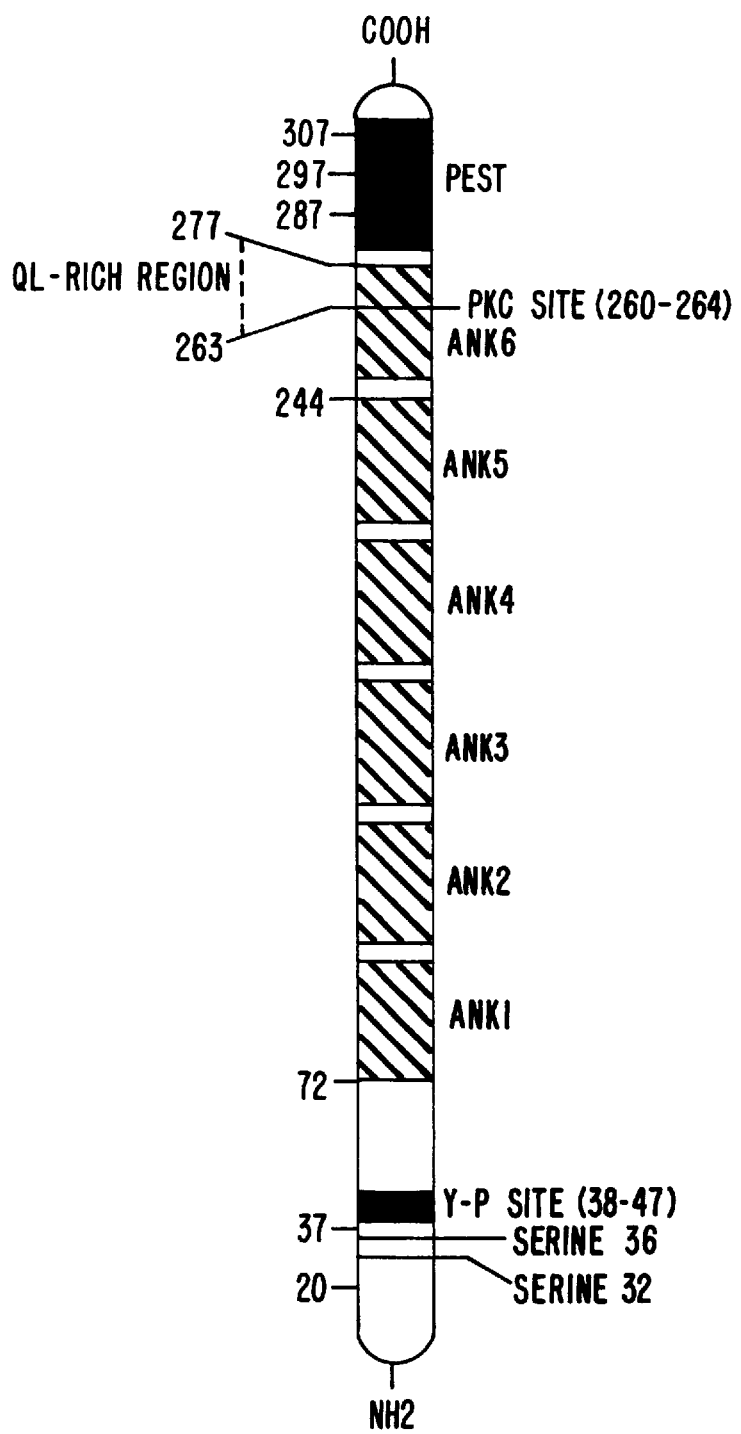
FIG. 2A is a schematic summary of human IκBα. The N-terminal portion of IκBα flanking the ankyrin repeats contains two notable regions including two serines at position 32 and 36 (DSGLDS) (SEQ ID NO: 1) and a consensus tyrosine phosphorylation site (Y-P site, KDEEYEQMVK) (SEQ ID NO: 2) between residues 38–47. The C-terminal region (277–317) contains the PEST (SEQ ID NO: 3) sequences (PEST (SEQ ID NO: 3) residues) and a small adjacent region (263–277) rich in glutamine (Q) and leucine (L) residues (QL-rich region), which overlaps with the sixth ankyrin repeat. The six ankyrin repeats are shown in hatched boxes (Ank1 to Ank6). Amino acid numbers are indicated above the map and reflect the end points of the various truncation mutants of IκBα examined.

To define the IκBα sequences required for its inducible degradation by TNF-α, a set of N-terminal deletion mutants was generated and inserted into a pCMV4-HA expression vector. This vector was constructed by inserting a PCR amplified DNA fragment encoding three copies of the influenza hemagglutinin (HA) epitope tag into the MluI and HindIII sites of the pCMV4 eukaryotic expression vector (Andersson et al. *J. Biol. Chem.* 264:8222–8229 (1989)). The termini of these IκBα deletion mutants were selected on the basis of potentially interesting sequences or residues identified within the primary IκBα sequence (FIG. 2A).

Figure 2B:
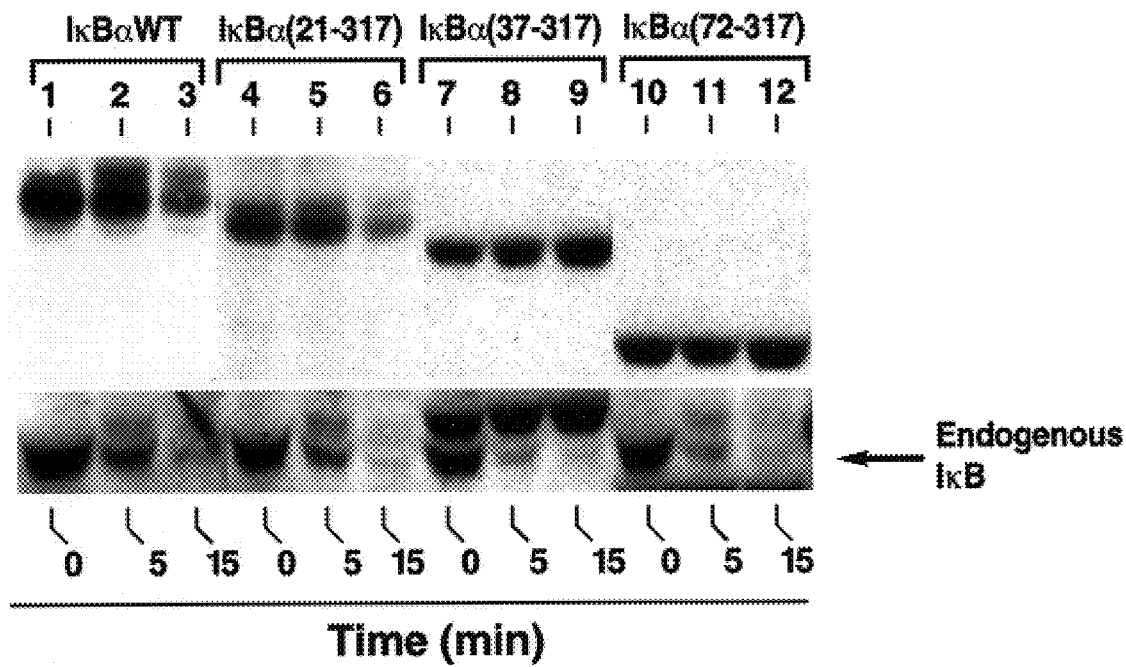
FIG. 2B depicts immunoblotting analysis of IκBα N-terminal truncation mutant degradation in transfected HeLa cells stimulated with TNF-α. HeLa cells were transfected with 2 μg of the cDNA expression vectors encoding either the wild-type IκBα or its various N-terminal truncation mutants as indicated. The cells were then stimulated with TNF-α (20 ng/ml) for the indicated time period. Cell extracts prepared and subjected to immunoblotting analysis using either anti-HA (upper panel) or anti-IκBα (lower panel). Degradation of endogenous IκBα present in the same extract is shown. The prominent non-degrading band appearing in lanes 7–9 of the endogenous IκBα control lane represents the epitope tagged N-terminal deletion mutant of IκBα which migrates similarly to wild-type IκBα. This mutant, like endogenous IκBα, is immunoprecipitated by the anti-C-terminal IκBα antibody used in these studies.

The N-terminal sequence flanking the ankyrin-rich domain of IκBα is notable for the presence of two neighboring serines (DS site, DSGLDS (SEQ ID NO: 1)), and a potential tyrosine phosphorylation site (PTK site, amino acids 39–47). Truncation mutants were generated to evaluate the potential function of these sites as well as other N-terminal sequences. Deletion of the first 20 amino acids of IκBα (IκBα(21–317)) produced no inhibitory effect on the degradative response induce by TNF-α (FIG. 2B, upper panel, lanes 4–6). In contrast, deletion to residue 37 (IκBα (37–317)) or 72 (IκBα(72–317)) completely abolished TNF-α induced degradation (upper panel, lanes 7–12). Based on homogeneous mobility, neither IκBα(37–317) or IκBα(72–317) appeared to undergo a TNF-α induced phosphorylation. Under these conditions, the endogenously expressed IκBα present in the same extracts was efficiently degraded in all the transfectants (lower panel, lanes 1–12), indicating that failure of these transfected IκBα mutants to respond to TNF-α stimulation was due to their lack of N-terminal sequences. Furthermore, the diminished degradation of the N-terminal deletion mutants of IκBα was not simply due to a modest change in the kinetics of breakdown, since these mutants remained fully intact after 45 minutes of TNF-α stimulation. Thus, the N-terminal boundary of the domain required for IκBα degradation mapped to the 16 amino acid region located between amino acids 21–36. This region contains two neighboring serines located at residues 32 and 36. To test more fully the involvement of these serine residues in the inducible phosphorylation and degradation of IκBα, site-directed mutagenesis was performed replacing either one (ser36) or both of these serines with alanine.

Figure 2C:
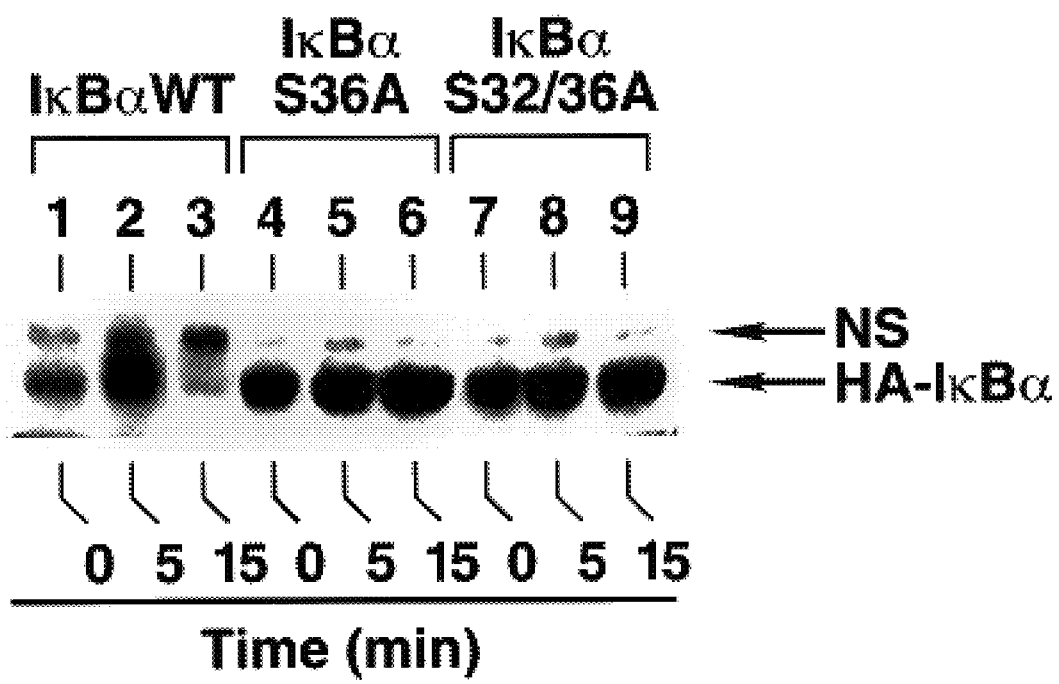
FIG. 2C depicts immunoblotting analysis of IκBα site directed mutants S36A and S32/36A. HeLa cells were transfected with cDNA expression vectors encoding either the wild-type IκBα (WT) or mutated versions of IκBα with an alanine for serine substitution at residue 36 (S36A) or residues 32 and 36 (S32/36A). After TNF-α stimulation, the cell extracts were subjected to immunoblotting using anti-HA as described in FIG. 1.

As shown in FIG. 2C, although the wild type IκBα was efficiently degraded in response to TNF-α stimulation (lanes 1–3), mutation of either ser36 or both ser32 and ser36 to alanine abolished this response (lanes 4–9). Furthermore, the double mutant failed to produce a phosphorylated form of IκBα (lanes 7–9). Using different conditions of electrophoresis than presented in this figure, IκBα S36A was found to yield a modified band migrating more rapidly than the band generated by TNF-α induction of wild-type IκBα. Thus, TNF-α induced degradation of IκBα appears to be regulated by phosphorylation events occurring at these two N-terminal serine residues.

These results, demonstrating that the N-terminal IκBα deletion mutants IκBα(37–317) and IκBα(72–317) retained full inhibitory function but failed to undergo degration in response to TNF-α stimulation suggested that such mutants would function as dominant negative repressors of NF-κA. To test this possibility, Jurkat T cells were transfected with the HIV κB luciferase reporter plasmid either alone or in combination with IκBα or the N-terminal IκBα deletion mutants 37–317 or 72–317. The recipient cells were then either untreated or incubated for 5 hr with TNF-α followed by isolation of cell extracts for luciferase assay (FIG. 7). As expected, in the absence of IκBα, TNF-α potently stimulated (about 35 fold) κB-directed luciferase gene expression (FIG. 7, column 1, open bar). The transfection of wild-type IκBα moderately inhibited this response (column 2). However, the stimulatory effects of TNF-α were completely abrogated in the presence of either of the two N-terminal truncation mutants of IκBα (columns 3 and 4, open bars). Apparently, by virtue of their ability to bind to and sequester Rel A in the cytoplasm but not to undergo TNF-α induced degradation (FIGS. 2B, 4, 5, and 6), both of these N-terminal deletion mutants of IκBα functioned as potent dominant negative repressors of NF-κB.

Figure 3:
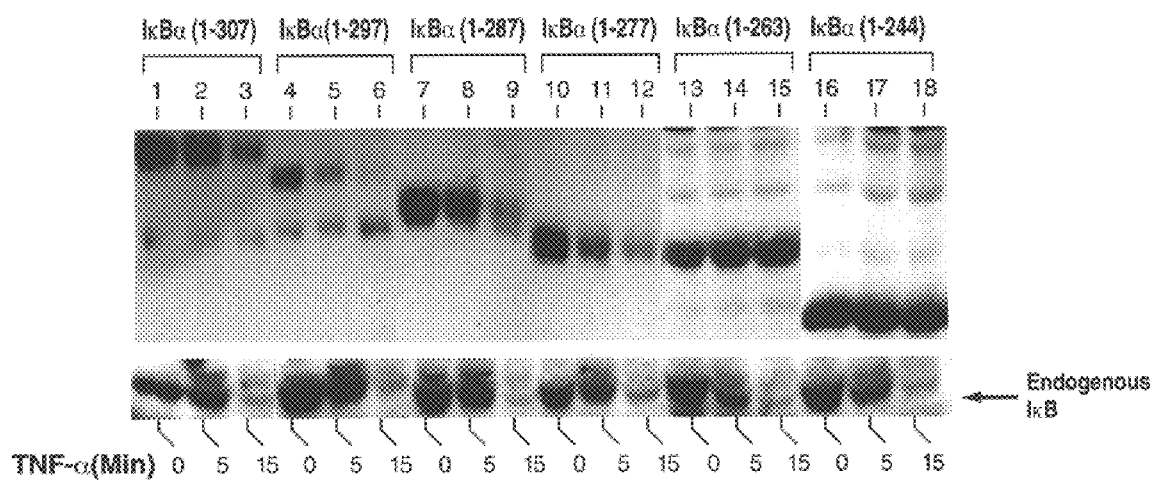
FIG. 3 depicts immunoblots of HeLa cells transfected with the indicated C-terminal truncation mutants of IκBα. After TNF-α stimulation, cell extracts were prepared and subjected to immunoblotting as described in the legend of FIG. 1. TNF-α induced degradation of the endogenous IκB present in these same extracts is also shown.

One of the striking features of IκBα is the presence of a C-terminal region that is rich in the amino acids proline, glutamic acid, serine, and threonine (PEST). To examine the potential role of these PEST sequences in TNF-α induced degradation, sequential 10 amino acid deletions were introduced in the C-terminus of IκBα. Each of these C-terminal deletion mutants was then tested for TNF-α induced degradation in HeLa cells. Sequential degradation of the final 40 amino acids which encompass the entire PEST sequences (see FIG. 2A) failed to alter the TNF-α induced degradation (FIG. 3, lanes 1–12). In contrast, further deletion of a 13 amino acid sequence located at the end of the sixth ankyrin repeat (amino acids 264–276) and distinguished by the presence of multiple glutamine and leucine residues (QL-rich region, FIG. 2A), yielded an IκBα analog (IκBα (1–263)) that failed to undergo TNF-α induced degradation (FIG. 3, lanes 13–15). Despite failing to undergo such inducible proteolysis, this IκBα mutant was present in the cytoplasm normally phosphorylated, suggesting that the QL region subserved a distinct and perhaps downstream function in this degradation pathway.

Figure 4:
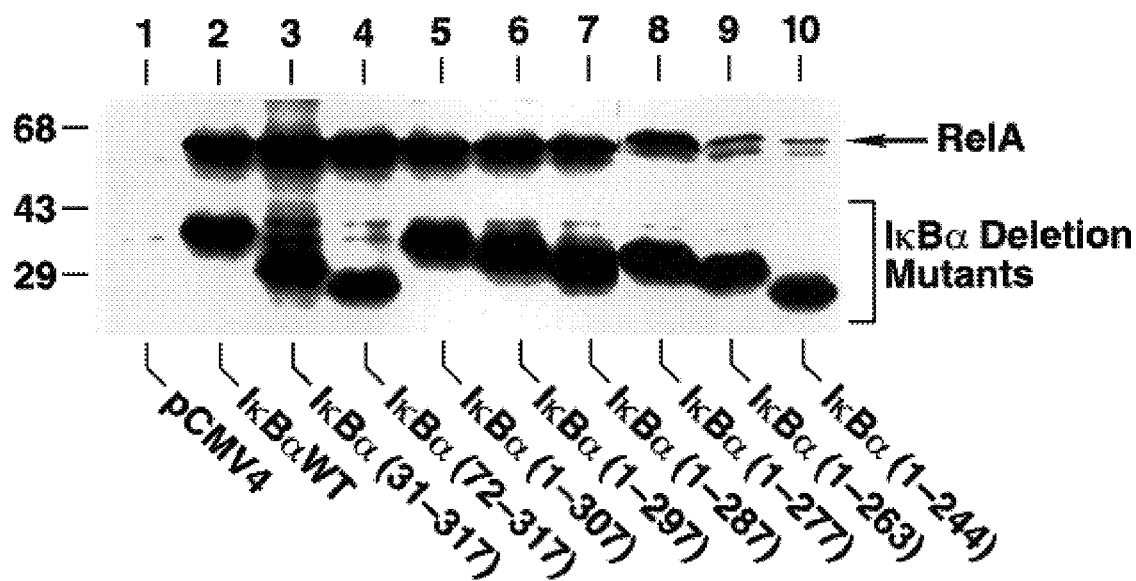
FIG. 4 depicts analyses of N- and C-terminal sequences needed for the physical association of IκBα with Rel A. COS7 cells were transfected with the Rel A cDNA expression vector together with the indicated IκBα expression vectors or the parental pCMV4 vector. The transfected cells were metabolically radiolabeled with $^{35}$S-methionine and $^{35}$S-cysteine, followed by the preparation of cell extracts. These extracts were then subjected to co-immunoprecipitation analysis using peptide-specific antibodies specific for either the C-terminus (lanes 1–4) or the N-terminus (lanes 5–10) of IκBα. The migration of IκBα and its mutants as well as the co-immunoprecipitated Rel A are indicated on the right.

Studies were then performed to examine whether the sequences regulating the inducible degradation of IκBα were also required for IκBα inhibition of NF-κB. First, the capacity of various IκBα mutants to bind to and co-immunoprecipitate with Rel A was analyzed. The expression vectors encoding each of the IκBα mutants were co-transfected into COS7 cells with a cDNA expression vector encoding Rel A (FIG. 4, lanes 2–10). As a control, Rel A was co-transfected with the parental vector (pCMV4) which lacks a cDNA insert (lane 1). After transfection, the cells were metabolically radiolabeled with $^{35}$S-methionine and $^{35}$S-cysteine and subjected to immunoprecipitation analysis with peptide-specific antisera reactive with either the C-terminus (lanes 1–4) or the N-terminus (lanes 5–10) of IκBα. As shown in FIG. 4, these antisera specifically immunoprecipitated both the 37 KD wild-type IκBα (lane 2) and all of the various IκBα deletion mutants (25–27 KD, lanes 3–10), but failed to react with Rel A alone (lane 1). Furthermore, as expected, Rel A was co-immunoprecipitated with wild-type IκBα (lane 2), suggesting the formation of stable complex between IκBα and this NF-κB subunit. Co-immunoprecipitation experiments also revealed that deletion of the entire N-terminal region (amino acids 1–71) or the C-terminal PEST(SEQ ID NO: 1)-like sequences (amino acids 278–317) of IκBα had no marked effect on its physical association with Rel A (lanes 3–8). However, further deletion of a 13-amino acid element between residues 277 and 263 corresponding to the QL rich region or beyond to the beginning of the sixth ankyrin repeat (1–244) significantly diminished the binding of IκBα to Rel-A (lanes 9 and 10). Thus, although the N-terminal region and the C-terminal PEST sequences appear largely dispensable for the binding of IκBα to Rel A, the QL-rich region appears required for association with Rel A as well as inducible degradation of IκBα.

Figure 5:
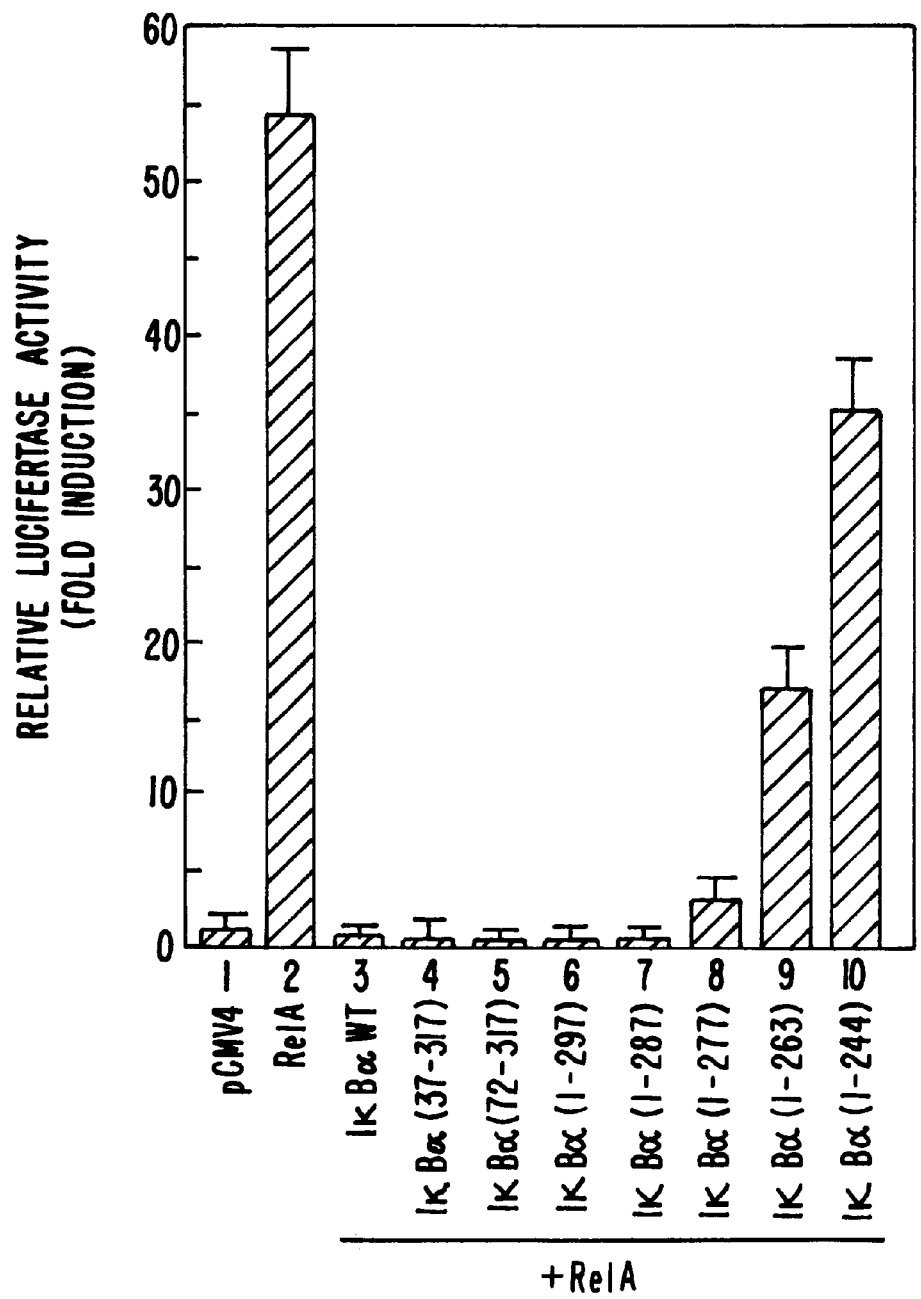
FIG. 5 depicts mapping of IκBα sequences required for inhibition of Rel A mediated transcriptional activation.

To explore the biological function of each of the IκBα mutants, human Jurkat T cells were co-transfected with an expression vector encoding Rel A and HIV-κB luciferase reporter plasmid (κB-TATA-luc). As shown in FIG. 5, in the absence of IκBα, Rel A potently stimulated the κB-directed transcription (about 55 fold, column 2) relative to background luciferase level obtained with the parental pCMV4 vector (column 1). As expected, Rel A mediated activation of the κB enhancer was completely inhibited when cells were co-transfected with wild-type IκBα expression vectors (column 3). Consistent with the co-immunoprecipitation studies, the N-terminal deletion mutants, which retained the ability to associate with Rel A, exhibited full inhibitory function (columns 4 and 5). Deletional analyses within the C-terminal portion of IκBα revealed that removal of the final 30 amino acids (IκBα(1–287)) had no effect on IκBα inhibitory function (column 7). Further deletion of 10 additional amino acids (IκBα(1–277)), which removed the entire PEST (SEQ ID NO: 3) or acidic region, modestly compromised IκBα inhibiting of Rel A (column 8). However, deletion to residue 263, which removes the QL-rich region or beyond (IκBα(1–244)) produced a marked loss of IκBα inhibitory function (columns 9 and 10). These findings were consistent with the inefficient physical association of the mutants with Rel A (FIG. 4, lanes 9 and 10). Taken together, the QL-rich region appears to be importantly involved in the regulation of Rel A functional activity as well as the inducible degradation of this inhibitor. In contrast, the N-terminal domain 21–36, which is required for inducible degradation due to serine phosphorylation at positions 32 and/or 36 is fully dispensable for IκBα inhibition of Rel A function. The PEST (SEQ ID NO: 3) sequences are not required for physical association, but their removal very modesty inhibits IκBα regulation of Rel A.

Parallel immunofluorescence assays were performed to localize Rel A expression in the presence of various IκBα mutants (FIG. 6). These studies indicated that inhibition of Rel A mediated transactivation by the various functional IκBα mutants precisely correlated with the ability of these mutants to block nuclear translocation of Rel A (FIG. 6, a–g). In brief, deletion of N-terminal sequences of IκBα (72–317, panel c), or removal of the C-terminal PEST (SEQ ID NO: 3) sequence (1–277, panel e) did not alter the largely cytoplasmic pattern of Rel A localization. In sharp contrast, deletion of the QL region (1–263, panel f) or all of the sixth ankyrin repeat (1–244, panel g) resulted in a predominantly nuclear pattern of Rel A expression. Together, these deletional analyses indicated that a 13-amino acid sequence element, located at the C-terminus of the sixth ankyrin repeat and rich in glutamines and leucines, is necessary for IκBα assembly with Rel A and for inhibition of Rel A action. In contrast, the entire N-terminal sequences and the C-terminal PEST (SEQ ID NO: 3) sequences flanking the ankyrin repeats appear dispensable for these inhibitory functions of IκBα on Rel A.

All references cited herein are specifically incorporated by reference in their entirety.

What is claimed is:

1. A composition comprising a nucleic acid molecule and a carrier, wherein the nucleic acid molecule encodes an IκBα polypeptide, wherein only residues 1 through 36 of the polypeptide are deleted, and wherein the polypeptide has a dominant negative phenotype.

2. A composition comprising a nucleic acid molecule and a carrier, wherein the nucleic acid molecule encodes an IκBα polypeptide, wherein only Ser32, Ser36, or both Ser32 and Ser36 of the polypeptide are deleted or substituted with another amino acid, and wherein the polypeptide has a dominant negative phenotype.

3. A composition comprising a nucleic acid molecule and a carrier, wherein the nucleic acid molecule encodes an IκBα polypeptide. wherein Ser32, Ser36, or both Ser32 and Ser36 of the polypeptide are deleted or substituted with another amino acid, wherein the polypeptide has a dominant negative phenotype, and wherein the C-terminus of the IκBα polypeptide has been deleted up to about residue 278.

4. The composition of claim 2 wherein the Ser32 and Ser36 of the polypeptide are both substituted with Ala.

5. A composition comprising a nucleic acid molecule and a carrier, wherein the nucleic acid molecule encodes an IκBα polypeptide, wherein only residues 1 through 36 and 278 through 317 of the polypeptide are deleted, and wherein the polypeptide has a dominant negative phenotype.

* * * * *

UNITED STATES PATENT AND TRADEMARK OFFICE
CERTIFICATE OF CORRECTION

PATENT NO.    : 6,180,772 B1
DATED         : January 30, 2001
INVENTOR(S)   : Greene et al.

It is certified that error appears in the above-identified patent and that said Letters Patent is hereby corrected as shown below:

Title page,
In the title, delete "NEGATIVE", and insert therefor -- POSITIVE --.

Column 4,
Line 55, delete "Geheration", and insert therefor -- Generation --

Column 10,
Line 22, delete ".", and insert therefor -- , --

Signed and Sealed this

Eleventh Day of December, 2001

Attest:

NICHOLAS P. GODICI
Attesting Officer    Acting Director of the United States Patent and Trademark Office

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Asp Ser Gly Leu Asp Ser
1               5

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS:
      (D) TOPOLOGY: linear (ii) MOLECULE TYPE: peptide -continued (xi) SEQUENCE DESCRIPTION: SEQ ID NO:2:

Lys Asp Glu Glu Tyr Glu Gln Met Val Lys
1               5                   10

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Pro Glu Ser Thr